(12) United States Patent
Bukowski

(10) Patent No.: US 12,376,591 B2
(45) Date of Patent: Aug. 5, 2025

(54) ANTIMICROBIAL ADDITIVE

(71) Applicants: GWD GLOBAL, INC., Garson City, NV (US); Wojciech Bukowski, Otwock (PL)

(72) Inventor: Wojciech Bukowski, Otwock (PL)

(73) Assignees: Wojciech Bukowski, Otwock (PL); GWD GLOBAL, INC., Carson City, NV (US)

( * ) Notice: Subject to any disclaimer, the term of this patent is extended or adjusted under 35 U.S.C. 154(b) by 0 days.

(21) Appl. No.: 15/774,899

(22) PCT Filed: Nov. 8, 2016

(86) PCT No.: PCT/PL2016/000123
§ 371 (c)(1),
(2) Date: May 9, 2018

(87) PCT Pub. No.: WO2017/082745
PCT Pub. Date: May 18, 2017

(65) Prior Publication Data
US 2018/0317483 A1    Nov. 8, 2018

(30) Foreign Application Priority Data
Nov. 9, 2015 (PL) .......................... 414732

(51) Int. Cl.
*A01N 43/42* (2006.01)
*A01N 25/00* (2006.01)

(52) U.S. Cl.
CPC ............. *A01N 43/42* (2013.01); *A01N 25/00* (2013.01)

(58) Field of Classification Search
CPC ................................ A01N 25/00; A01N 43/42
See application file for complete search history.

(56) References Cited

U.S. PATENT DOCUMENTS

| | | | |
|---|---|---|---|
| 4,459,409 A * | 7/1984 | Ladner | A01N 43/42 546/168 |
| 4,482,538 A * | 11/1984 | Davies | A61Q 3/02 106/169.56 |
| 4,789,692 A | 12/1988 | Rei et al. | |
| 7,361,719 B2 | 4/2008 | Moon et al. | |
| 7,435,771 B2 * | 10/2008 | Lei | C09D 5/1687 524/287 |
| 2010/0239509 A1 * | 9/2010 | Chodorowski-Kimmes | A61K 8/85 424/59 |
| 2011/0212333 A1 * | 9/2011 | Maliverney | C09D 5/1687 428/447 |

FOREIGN PATENT DOCUMENTS

| | | |
|---|---|---|
| CN | 10 453 1133 A | 4/2015 |
| CN | 10 500 1032 A | 10/2015 |
| DE | 193 2 415 A1 | 1/1970 |
| EP | 0 126 893 A1 | 5/1984 |
| GB | 988 483 | 4/1965 |
| JP | 15 2236 A | 8/2014 |
| PL | 187979 B1 | 11/2004 |
| WO | WO 01/37666 A2 | 5/2001 |
| WO | WO-2014055418 A1 * | 4/2014 ............... B05D 3/12 |

OTHER PUBLICATIONS

Cooper. Poisonous plants in Britain and their effects on animals and man., 1984, xiv + 305pp. ref. 46pp (Year: 1984).*
Langley. Wilderness and Environmental Medicine, 8, 8-16 (1997) (Year: 1997).*
Newby. Progress in Organic Coatings 56 (2006) 135-145) (Year: 2006).*
Resources, Conservation and Recycling 47 (2006) 209-221 (Year: 2006).*
P P Sambaveka. et al. In-silico, in-vitro antibacterial activity and toxicity profile of new quinoline derivatives. Indian J. of Chem. 52B, Dec. 2013, pp. 1521-1526.
Hozer, L. et al. (1927), Synthesis and Derivatives of Acridine Acid. J. Prakt. Chem., 116: 43-56.
Chammanee, P., et al. Effects of Anti-Bacterial Agents, Sample Preparation and Contact Time on Anti-Bacterial Efficacy in MDPE Film. J. of Macro. Sci., Part B, 48(4), 755-765.
Lee, CH., et al. Growth inhibiting activity of quinaldic acid isolated from Ephedra pachyclada against intestinal bacteria. J. Korean Soc. Appl. Biol. Chem. 52, 331-335 (2009).
Moghadamtousi SZ, et al.A review on antibacterial, antiviral, and antifungal activity of curcumin. Biomed Res Int. 2014:186864. Epub Apr. 29, 2014.
Taptim, K. Mechanical properties and antimicrobial performance evaluations for silicone rubber compounds. Intl Conference on Materials Processing Technology Jun. 2011 1-7.
Smirnova IN, et al. Inhibition of yeast glyceraldehyde-3-phosphate dehydrogenase by nicotinic and quinolinic acid derivatives . . . Dokl Akad Nauk SSSR. 1973;210(6):1471-3.

* cited by examiner

*Primary Examiner* — Kortney L. Klinkel
*Assistant Examiner* — Richard Grant Peckham
(74) *Attorney, Agent, or Firm* — Andrzej Malarz, Esq.

(57) ABSTRACT

The subject of the invention is an antibacterial and antifungal preparation constituting an additive to various materials, in particular, to plastics, containing no nanometal particles, which may be combined with almost any kind of polymers or other materials, from biodegradable polymer packaging, textiles, paints, to hardened PVC, using any processing technology, such as: extrusion, injection moulding, blowing, pressing, lamination, pouring or pumping through capillaries in production of continuous fibre for the textile industry. The biocide contains an active ingredient in the form of a derivative of an acid with a formula shown in drawing 1, where R1 and R2 signify, carboxyl groups (—COOH), R3, R4, R5, R6, R7 signify hydrogen (H), X signifies nitrogen (N) and Y signifies carbon (C) in the amount of 60 to 85% by weight, and the remaining amount is a composition of inorganic and organic fillers.

3 Claims, 2 Drawing Sheets

ANTIMICROBIAL ADDITIVE

Figure 1:
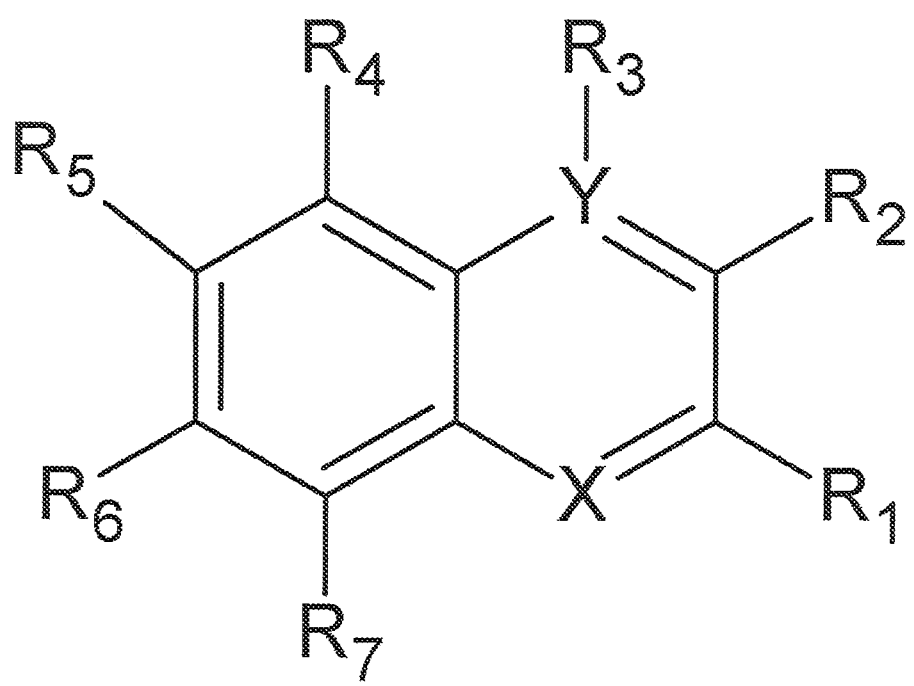
Figure 2:
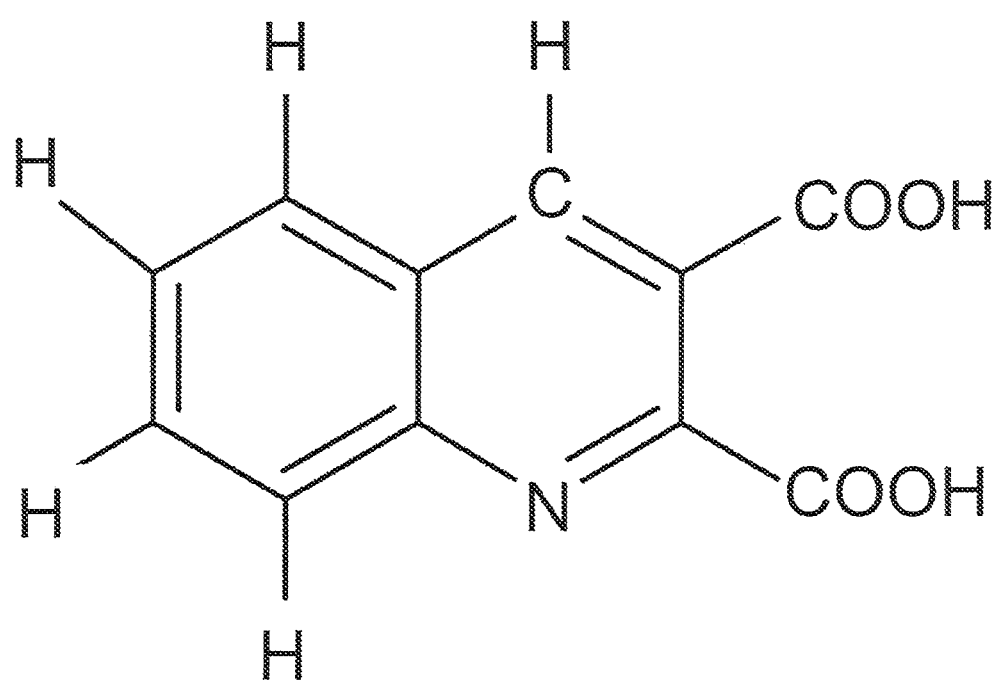

The subject of the invention is a preparation of organic origin, constituting an additive to materials and products requiring antibacterial and antifungal properties, not containing any nanometal particles. The developed preparation may be combined with almost every kind of polymers and other materials—from biodegradable polymer packaging, textiles, paints, to hardened PVC—using any processing technology, such as: extrusion, injection molding, blowing, pressing, lamination, pouring or pumping through capillaries in production of continuous fibre for the textile industry. The preparation is supposed to be added, for example, to plastics used for manufacturing of antimicrobial medical devices, vacuum containers for storage of food, packaging for foodstuffs, sealed vacuum packaging, kitchen cutting boards. It may also be used for manufacturing of other kitchen utensils, household appliances, air conditioners, water treatment devices, toys, for production of automobile components, office products, or clothing products and footwear. It may constitute an additive to paints, varnishes, textiles and other similar products. The invention also discloses the active ingredient utilized in the preparation.

Known from the German patent description with the application number DE I 932 415 (application of 26 Jun. 1969), is an invention disclosing a new group of molecular compounds of salts formed as a result of addition of sorbic acid, which may be formed through connection with a molecule of chlorine, bromine or iodine. The substance described therein has fungicidal and yeasticidal properties, utilized in protection of fruit trees and seeds as well as foodstuffs.

An invention is also known from the English patent description EN-988,483 (claim of 11 Feb. 1963), disclosing sulphate salt of 5-methyl-8-hydroxy-quinoline. It is obtained as a solution of sulphate in a solution of hydrochloric acid and quinoline. This substance has bacteriostatic and bactericidal properties.

Another invention "Mould Control Agent" is known from the Polish patent description, patent no. PL-187979 (published: BUP 18/1999 of 30 Aug. 1999), disclosing a mould control agent containing, as the biologically active ingredient, a mixture of copper bis(8-quinolinolate) in the amount of 5 to 80% by weight with a bis-thiocarbamyl polysulphide derivative with a formula shown in the drawing, where $R_1$, $R_2$, $R_3$ and $R_4$ are identical and signify a methyl or ethyl group, and "n" signifies an integer "1" or "2", particularly with tetramethylothiuram disulphide in the amount of 20 to 95% by weight.

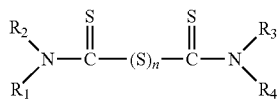

The agent may be applied as an additive to finishing materials in the construction industry.

Another solution has been known, disclosed in a description of the Polish patent claim P-355623 (published: BUP 9/2004 of 4 May 2004) "Combinations of fungicidal active ingredients". The fungicide presented therein contains a combination of active ingredients, consisting of A) 8-t-butyl-2-(N-ethyl-N-n-propylamine)metylo-1,4-dioxaspiro [5,4]decan with a formula (1) (=spiroxamine) and B) 1-(4-chlorophenyl)-4,4-dimethyl-3-(1,2,4-triazol-1-ylmethyl) pentan-3-ol with a formula (II) (=tebuconazole) as well as C) 5,7-dichloro-4-(4-fluorophenoxy) quinoline with a formula (III) (=quinoxyfen).

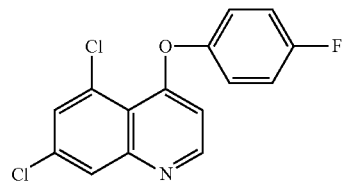

Known from the US patent description, patent no. U.S. Pat. No. 4,789,692 (Appl. No. 897,760), is an invention "Resin-immobilized biocides" disclosing a solid biocide resin concentrate for supplying to an end use resin composition, of which a primary thermoplastic resin comprises a major proportion, comprising a biocide in an amount which is effective to protect the resin composition from an microorganism attack, the solid biocidal resin concentrate comprising a first thermoplastic resin identical to or substantially identical to said primary thermoplastic resin, said primary thermoplastic resin being incompatible with stable incorporation of said biocide at 20 times end use concentration, an alloyed second thermoplastic resin and a biocide, selected from the group consisting of 10,10-oxybisphenoxazine and its derivatives, N (2-methyl-1-naphthyl) maleimide and 2-octyl-4-isothiazolin-3-one, stably incorporated and immobilized in the said alloyed resins at a concentration of at least 20 times end use concentration. Said first thermoplastic resin is selected from the group consisting polyethylene, nylon, polystyrene, polyvinyl chloride, polycarbonates, polypropylene, polyvinyl chloride/polyvinyl acetate copolymer, polyvinyl, acetate, polymethyl and methacrylate, and if said first thermoplastic resin is polyethylene, said second resin is selected from the group consisting of ethylene/acrylic acid copolymer, polypropylene, polystyrene, polyvinyl chloride/polyvinyl acetate copolymer, polyacrylic acid, ethylene/vinyl acetate/carbon monoxide terpolymer; and if the first thermoplastic resin is selected from the group consisting of nylon, polystyrene, polyvinyl chloride, polycarbonate, polypropylene, polyvinyl chloride/polyvinyl acetate copolymer, polyvinyl acetate, polymethyl methacrylate, said second thermoplastic resin is selected from the group consisting of ethylene/acrylic acid copolymer and ethylene/vinyl acetate/carbon monoxide terpolymer.

Known from US patent description U.S. Pat. No. 7,361, 719 (Appl. No. 503,040), is an invention "Monomer with anti-microbial character, polymer using the same, and manufacturing method thereof", disclosing an anti-microbial acrylic copolymer with a molecular weight of 10 000-1 000 000, described with the formula disclosed in the invention; whereas, one of substituents in this case is a C1-C13 alkane group comprising one or more selected from the group consisting of esters, carbonyl group, amide, amine, cycloalkyls, ether, hydroxyl group, carboxylic acid, C2-C10 hetero ring containing N or O, sulpho group, silane, lactone and aldehyde groups.

Another antibacterial agent, containing a quinoline derivative, was described in a US paper published in the "Journal of Mononuclear Science part B: PHYSICS" (No. 48:755-765, 2009 ISSN 00222348, print: N5 25-609 IX) "Effects of Anti-Bacterial Agents, Sample Preparation and Contact Time on Anti-Bacterial Efficacy in MDPE Film". It discussed the antibacterial efficacy of medium-density polyethylene (MDPE) with various contents of different antibacterial agents, depending on the antibacterial concentration, size and form of the sample, MDPE, and the contact time, whereas three different of antibacterial agents were used, namely: (a) carbendazim and zinc dimethyl dithiocarbamate, (b) 2-hydroxypropyl-3-piperazinyl-quinoline carboxylic acid methacrylate and silver substituted zeolite. In order to assess the antibacterial efficacy, the most widespread microbes, *Escherichia coli* (*E. Coli*) ATCC 29214 and *Staphylococcus aureus* (*S. aureus*) ATCC 73565, were selected as Gram-negative and Gram-positive.

In June 2011, during the International Conference on Material Processing Technology (2011 Jun. 2-3, Phuket, THAILAND), materials have been presented concerning assessment of mechanical and antibacterial properties of silicone rubber mixtures with an addition of the BIO-CLEANCT substance: (2-Hydroxypropyl-3-Piperazinyl-Quinoline-Carboxylic Acid Methacrylate [HPQM]), displaying bactericidal and fungicidal properties.

Biostatic agents, sometimes referred to as "antimicrobials", will be used in many applications of plastics and in various industries. Products containing a bacteriostatic additive are characterized by many advantages, the most important of which is prevention of development of fungi and bacteria. The increasing possibilities for spread of diseases create demand for antibacterial chemicals for use in industry, medicine and consumer goods, as well as in the food industry. The problem so far was development of a preparation which would reduce transmission of infectious diseases and bacteria or various fungi types, and would simultaneously not contain any toxic substances harmful to health. The known and used preparations release toxic chemical compounds which may cause cancer and infertility. The increasing easiness of transmission of diseases increases the risk of spread thereof and necessitates development of substances inhibiting this phenomenon. Efforts oriented towards containing the transmission of infectious diseases (including AIDS) provide a stimulus for search for increasingly new and more efficient agents to protect the universally used substances and materials as well as food.

The goal of the invention is to develop a preparation with antibacterial and antifungal properties, which will have no harmful properties of substances known hitherto, often containing nanometal particles, and simultaneously, a preparation containing a substance with antibacterial and antifungal properties, which may be incorporated in various substances: plastics, resins, fibers, paints, varnishes, protective preparations, as well as other substances at various processing stages.

During the conducted research, it was incidentally stated that an agent containing a derivative of 2,3-quinoline dicarboxylic acid with a formula shown in the drawing, where $R_1$ and $R_2$ signify, carboxyl groups (—COOH), $R_3$, $R_4$, $R_5$, $R_6$, $R_7$ signify hydrogen (H), X signifies nitrogen (N) and Y signifies carbon (C)—is a perfect antibacterial and antifungal agent, stable over time, effective already at small doses, and compatible with a multitude of types of plastics and other materials or compositions thereof.

The active ingredient will be known under the trade name "SEANTEX".

The antibacterial and antifungal preparation containing, beside the biologically active ingredient, auxiliary ingredients such as fillers, is characterized in that it contains a biologically active ingredient being a derivative of the acid with a formula 1 as shown in the drawing, in which $R_1$ and $R_2$ signify, carboxyl groups (—COOH), $R_3$, $R_4$, $R_5$, $R_6$, Ry signify hydrogen (H), X signifies nitrogen (N) and Y signifies carbon (C) in the amount of 60 to 85% by weight, and the remaining amount is a composition of inorganic, preferably silica and organic fillers, preferably benzoic acid.

Preferably, according to the invention, sodium benzoate is used as organic filler.

Preferably, curcumin is used as organic fillers in the preparation.

Preferably, chalk is used as inorganic fillers in the preparation.

The preparation is preferably introduced to a composition of plastics in an amount of 3-7%.

The preparation is preferably introduced to a composition of interior and exterior paints, varnishes and impregnations in the amount of 3-7%.

The preparation is preferably introduced to a composition of silicones and resins in the amount of 3-7%.

The preparation, according to the invention, contains 60 to 85% by weight of the active ingredient, and the remaining amount of the preparation comprises a composition of organic and inorganic fillers, namely, benzoic acid, sodium benzoate, curcumin, chalk, silica.

Curcumin is an organic chemical compound built of two feruloyl moieties connected with a carbon atom.

The developed antibacterial and antifungal preparation, the active ingredient of which will be available under the trade name "SEANTEX", is a biostatic additive of organic origin, containing no toxic compounds. The preparation satisfies the demand for products with an antibacterial effect, not containing any nanometal particles. This preparation inhibits the development of microorganisms. The conducted research has shown that the products manufactured using the developed agent effectively prevent the development of known bacteria, such as Bacillius *subtilis, Escherichia coli, Proteus mirabilis, Proteus vulgaris, Streptococcus pneumoniae, Salmonella* and many others, as well as fungi: *Candida albicans, Aspergillus niger, Penicillium ochrochloron*, and many others. Another advantage of the developed preparation is easiness of use, non-toxicity, excellent mechanical properties, as well as compatibility with new generation biodegradable plastics. This preparation is tolerant to heat. The application of the developed preparation enables prevention of stains and discolouration of coloured materials, caused by microorganisms, and inhibits the development and spread of substances causing an unpleasant smell and loss of the desired mechanical properties in industrial and commercial products. The developed compound may be used in any thermoplastic material forming method and added to any material processing device without a necessity of additional expansion or installation of additional equipment. Such simple integration with the already existing material production processes eliminates barriers for introduction of the developed preparation to the already implemented production without a necessity to make the production process more expensive.

An important advantage of the described composition—due to its possibility of being internally incorporated into the structure of a polymer—is the fact that this agent is environmentally neutral, both during its incorporation into polymers, e.g. thermoplastic ones, in the form of so-called masterbatch, and in the production process or during recycling. It is capable of being used to protect various thermoplastic polymers of LDPE, MDPE, HDPE, PP, P5, rubber, PCV, PLA, PET and others against *Escherichia coli* (ATCC 25922), *Staphylococcus aureus* (ATC 25 923) and other bacteria.

The preparation is characterized by considerable antibacterial efficacy, lack of nanometals and halogens, as well as the fact that an addition of this agent does not cause any reduction of whiteness index of the material, nor does it prevent colouring thereof.

A relatively low melting point of the active ingredient and a high boiling point facilitates application of the preparation in many market products.

Materials containing the preparation according to the invention are recyclable.

The invention has been disclosed in embodiments which, however, only illustrate the invention, not limiting the possible applications thereof.

EMBODIMENT NO. 1

A preparation containing 80% of the substance disclosed in the invention, under the trade name "SEANTEX", and 20% of inorganic fillers-chalk and silica in a ratio of 1:1. A preparation with such composition is added to latex paints in the amount of 5% per unit of mass, and the entire composite is mixed until totally homogenous.

Latex paints containing the preparation according to the invention are resistant to the effect of fungi and bacteria.

Tests for resistance to development of fungi and bacteria were carried out in accordance with Work Instruction JA/0074/R based on the methodology described in the standard ISO 22196.

The following samples were subject to analyses:
  sample "0"—reference paint;
  sample "1"—paint into which 3% of the preparation was introduced;
  sample "2"—paint into which 5% of the preparation was introduced.

Testing Method:
  Suspensions of strains were applied to samples with dimensions of 5×5 cm. The suspensions on the samples were covered by pieces of sterile PE foil with dimensions of 4×4 cm in order to spread the microorganisms evenly. The samples were incubated for 24 h at a temperature of 36° C. for bacteria and at a temperature of 22° C. for mould. Immediately after the occulation of the samples, suspension was rinsed from a part of the samples of the reference sample in order to determine the number of cells/spores at a time of 0 h. A similar procedure was followed after 24 hours of contact with the remaining samples of the reference sample and the tested sample.

The results were presented in tables below, by calculating the difference of logarithms from the number of cfu/ml recovered from the reference sample and the tested sample after the contact time.

Test Results and Assessment with Requirements
  $Log_{10}$ Reduction—a difference between the logarithm of the average cfu number on the reference samples after 24 h and the logarithm of the average cfu number on the tested samples.

Bacterial Strain—*Staphylococcus aureus*

| Sample | Repetition | Cell count/ cm³ | Geom. mean of Cell count/cm³ | $Log_{10}$ of Cell count/ cm² | Average $Log_{10}$ of Cell count/ cm² | $Log_{10}$ Reduction |
|---|---|---|---|---|---|---|
| | 1 | 1.7E+0.4 | | 4.23 | | |
| Ref. | 2 | 1.5E+0.4 | 1.4E+0.4 | 4.17 | 4.16 | |
| t = 0 h | 3 | 1.2E+0.4 | | 4.09 | | |
| | 1 | 5.0E+0.4 | | 4.70 | | |
| Ref. | 2 | 6.3E+0.4 | 6.35E+0.4 | 4.80 | 4.80 | |
| 24 h | 3 | 8.3E=0.4 | | 4.92 | | |
| | 1 | <1.0E+0.1 | | 1.00 | | |
| Sample 1 | 2 | <1.0E+0.1 | <1.0E+0.1 | 1.00 | 1.00 | 3.80 |
| | 3 | <1.0E+0.1 | | 1.00 | | |
| | 1 | <1.0E+0.1 | | 1.00 | | |
| Sample 2 | 2 | <1.0E+0.1 | <1.0E+0.1 | 1.00 | 1.00 | 3.80 |
| | 3 | <1.0E+0.1 | | 1.00 | | |

Bacterial Strain—*Escherichia coli*

| Sample | Repetition | Cell count/ cm³ | Geom. mean of Cell count/cm³ | $Log_{10}$ of Cell count/ cm² | Average $Log_{10}$ of Cell count/ cm² | $Log_{10}$ Reduction |
|---|---|---|---|---|---|---|
| | 1 | 2.2E+0.4 | | 4.35 | | |
| Ref. | 2 | 2.3E+0.4 | 2.2E+0.4 | 4.35 | 4.34 | |
| t = 0 h | 3 | 2.1E+0.4 | | 4.33 | | |
| | 1 | 9.3E+0.4 | | 3.97 | | |
| Ref. | 2 | 4.4E+0.4 | 1.7E+0.3 | 2.64 | 3.23 | |
| 24 h | 3 | 1.2E=0.4 | | 3.09 | | |
| | 1 | <1.0E+0.1 | | 1.00 | | |
| Sample 1 | 2 | <1.0E+0.1 | <1.0E+0.1 | 1.00 | 1.00 | 2.23 |
| | 3 | <1.0E+0.1 | | 1.00 | | |
| | 1 | <1.0E+0.1 | | 1.00 | | |
| Sample 2 | 2 | <1.0E+0.1 | <1.0E+0.1 | 1.00 | 1.00 | 2.23 |
| | 3 | <1.0E+0.1 | | 1.00 | | |

Fungal Strain—Mould—*Cladosporium* Cladosporioides

| Sample | Repetition | Cell count/ cm$^3$ | Geom. mean of Cell count/cm$^3$ | Log$_{10}$ of Cell count/ cm$^2$ | Average Log$_{10}$ of Cell count/ cm$^2$ | Log$_{10}$ Reduction |
|---|---|---|---|---|---|---|
|  | 1 | 2.2E+0.4 |  | 4.34 |  |  |
| Ref. | 2 | 2.2E+0.4 | 2.2E+0.4 | 4.35 | 4.34 |  |
| t = 0 h | 3 | 2.2E+0.4 |  | 4.35 |  |  |
|  | 1 | 1.8E+0.4 |  | 3.26 |  |  |
| Ref. | 2 | 1.6E+0.4 | 1.64E+0.3 | 3.21 | 3.22 |  |
| 24 h | 3 | 1.5E=0.4 |  | 3.18 |  |  |
|  | 1 | <1.0E+0.1 |  | 1.00 |  |  |
| Sample 1 | 2 | <1.0E+0.1 | <1.0E+0.1 | 1.00 | 1.00 | 2.22 |
|  | 3 | <1.0E+0.1 |  | 1.00 |  |  |
|  | 1 | <1.0E+0.1 |  | 1.00 |  |  |
| Sample 2 | 2 | <1.0E+0.1 | <1.0E+0.1 | 1.00 | 1.00 | 2.22 |
|  | 3 | <1.0E+0.1 |  | 1.00 |  |  |

EMBODIMENT NO. 2

A preparation containing 70% of the active ingredient according to the invention and 30% of the composition of fillers: organic filler—17%, benzoic acid; inorganic filler—13%, silica, is mixed with PVC material in the form of masterbatch and introduced into the material in the amount of 3% by weight.

The composition of the material and the preparation was processed through thermoforming (extrusion) at the following parameters:

Screw rotation speed: 185 rpm
Head pressure: 11-15 bar
Mass temperature: 180° C.

The obtained product is highly resistant to development of bacteria and fungi.

EMBODIMENT NO. 3

A preparation containing 85% of the active ingredient according to the invention and 15% of the composition of fillers: organic filler—15% benzoic acid, is mixed with PP in the form of masterbatch and introduced into the material in the amount of 3% by weight.

The composition of the material and the preparation was processed through thermoforming (extrusion).

Screw rotation speed: 185 rpm
Head pressure: 12-16 bar
Mass temperature: 195° C.

The obtained product is highly resistant to development of bacteria and fungi.

The test for resistance to mould fungi of PP samples with an additive of the preparation was carried out in accordance with the standard PN-EN ISO 846.

Contaminated samples were incubated at the temperature of 29+1° C. for a period of 28 days. Relative humidity in the incubator chamber exceeded 90%.

Obtained Results:

| Samples | CD (+S) | CD (−S) |
|---|---|---|
| PP + 3% of the preparation | 0 | 0 |
| PP + 5% of the preparation | 0 | 0 |
| PP + 10% of the preparation | 0 | 0 |

The results of the conducted tests of biostatic efficacy of the agent disclosed in the invention prove that a preparation containing the "SEANTEX" substance has a beneficial effect of bio-protective nature.

The invention claimed is:

1. A preparation consisting of a biologically active ingredient and fillers, wherein the preparation is antibacterial and antifungal having the biologically active ingredient being a compound of formula 1 shown in the drawing,

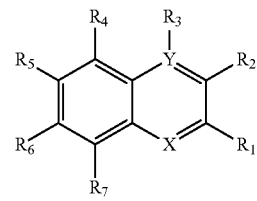

where $R_1$ and $R_2$ both signify carboxyl groups (—COOH), $R_3$, $R_4$, $R_5$, $R_6$, $R_7$ signify hydrogen (H), X signifies nitrogen (N) and Y signifies carbon (C) in an amount of 60 to 85% by weight, and a remaining amount is a composition of inorganic filler, wherein said inorganic filler is silica and organic filler, wherein said organic filler is benzoic acid, wherein the preparation is internally incorporated into a structure of a polymer during manufacture of a masterbatch, in a production process, or during recycling, wherein the preparation is used to protect thermoplastic polymers against *Escherichia coli* and *Staphylococcus aureus* bacteria, wherein the preparation contains no nanometal particles or halogens, wherein addition of the preparation to a polymer material does not cause any reduction of whiteness thereto, nor does it prevent colouring thereof, wherein a low melting point of the biologically active ingredient and a high boiling point of the biologically active ingredient facilitates application of the preparation in plastics, silicones, resins, fibers, paints, varnishes, impregnations or compositions thereof, wherein plastics, silicones, resins, fibers, paints, varnishes, impregnations or compositions thereof containing the preparation are recyclable, and wherein the preparation prevents development of bacteria or fungi harmful to human health.

2. The preparation according to claim 1, wherein the preparation is a part of a composition of plastics in an amount of 3-7% by weight.

3. The preparation according to claim 1, wherein the preparation is a part of a composition of silicones and resins in an amount of 3-7% by weight.

* * * * *

UNITED STATES PATENT AND TRADEMARK OFFICE
CERTIFICATE OF CORRECTION

Page 1 of 1

PATENT NO. : 12,376,591 B2
APPLICATION NO. : 15/774899
DATED : August 5, 2025
INVENTOR(S) : Wojciech Bukowski It is certified that error appears in the above-identified patent and that said Letters Patent is hereby corrected as shown below:

On the Title Page

Item (71), should read as follows:
-- (71) Applicants: GWD GLOBAL, INC., Carson City,
 NV (US); Wojciech Bukowski, Otwock (PL) --

Signed and Sealed this
Eleventh Day of November, 2025

John A. Squires
*Director of the United States Patent and Trademark Office*